United States Patent [19]

Drago et al.

[11] Patent Number: 5,578,027
[45] Date of Patent: Nov. 26, 1996

[54] METHOD AND SYSTEM FOR COLLECTING, PROCESSING, AND STORING BLOOD COMPONENTS

[75] Inventors: James A. Drago, El Sobrante; Bruce Kuhlemann, Hayward; Richard Spielberg, Yerba Linda, all of Calif.

[73] Assignee: Pall Corporation, East Hills, N.Y.

[21] Appl. No.: 466,614

[22] Filed: Jun. 6, 1995

Related U.S. Application Data

[62] Division of Ser. No. 123,521, Sep. 17, 1993, abandoned.

[51] Int. Cl.$^6$ .................................................. A61B 19/00
[52] U.S. Cl. ................. 604/408; 604/403; 128/DIG. 24; 128/DIG. 27
[58] Field of Search ................................. 604/403–404, 604/407–410; 128/898, DIG. 24, DIG. 27

[56] References Cited

U.S. PATENT DOCUMENTS

| | | | |
|---|---|---|---|
| 4,112,989 | 9/1978 | Grode et al. | 150/1 |
| 4,417,753 | 11/1983 | Bacehowski et al. | 285/21 |
| 4,425,177 | 1/1984 | Shinno . | |
| 4,460,366 | 7/1984 | Shinno . | |
| 4,490,420 | 12/1984 | Yoshida . | |
| 4,561,110 | 12/1985 | Herbert . | |
| 4,565,720 | 1/1986 | Yaeo et al. . | |
| 4,619,650 | 10/1986 | Wisdom | 604/408 |
| 4,657,341 | 4/1987 | Ichikawa et al. . | |
| 4,758,463 | 7/1988 | Vicik et al. . | |
| 4,851,272 | 7/1989 | Knox et al. . | |
| 4,994,021 | 2/1991 | Smith et al. | 604/409 |
| 5,088,994 | 2/1992 | Porat et al. . | |
| 5,095,054 | 3/1992 | Lay et al. . | |
| 5,104,702 | 4/1992 | Ohachi | 428/354 |

FOREIGN PATENT DOCUMENTS

| | | |
|---|---|---|
| 51-109950 | 9/1976 | Japan . |
| 58-89362 | 5/1983 | Japan . |
| 60-236749 | 11/1985 | Japan . |
| 60-236750 | 11/1985 | Japan . |
| 60-236752 | 11/1985 | Japan . |
| 62-122752 | 6/1987 | Japan . |
| 62-176841 | 8/1987 | Japan . |
| 62-271721 | 11/1987 | Japan . |
| 63-120643 | 5/1988 | Japan . |
| 63-216722 | 9/1988 | Japan . |
| 1-192535 | 8/1989 | Japan . |
| 1-57673 | 12/1989 | Japan . |
| 2-50836 | 2/1990 | Japan . |
| 2-81628 | 3/1990 | Japan . |
| 2-42067 | 9/1990 | Japan . |
| 2-255752 | 10/1990 | Japan . |
| 3-78258 | 12/1991 | Japan . |

OTHER PUBLICATIONS

Doglietto et al., "Insulin Adsorption to Three–Liter Ethylen Vinyl Acetate Bags during 24–Hour Infusion", *J. of Parenteral and Enteral Nutrition* 13(5):539–541 (1989).

Hansen et al., "Intrinsic and Extrinsic Microbial Contamination of Home Total Parenteral Nutrition Manufactured in Eva–Infusion Bags (the I.V. Bag®)", *J. Clin. Pharm. & Ther.* 12:325–331 (1987).

Kouketsu et al., "Storage of Apheresis Platelets in Ethylene–Vinyl Acetate Copolymer Bags: Relationship Between the Bag Size and the Number of Platelets Maintaining Aerobic Metabolism", *Cryobiology* 25:440–444 (1988).

*Primary Examiner*—John G. Weiss
*Assistant Examiner*—P. Zuttarelli
*Attorney, Agent, or Firm*—Leydig, Voit & Mayer

[57] ABSTRACT

Apparatus and method for collecting, processing, and storing blood components, such as plasma. The method involves collecting the blood component in a flexible storage bag manufactured from ethylene vinyl acetate EVA, having a composition of between about 9% and about 18% vinyl acetate by weight of total EVA co-polymer. The EVA bag is sealed, and the sample is frozen in the bag at a temperature of at least as low as –30° C. to form a substantially solid pellet contained in the storage bag. The bag then is fractured and the pellet is removed in its intact, frozen form. The co-polymer bag may have an inner surface with an etched or embossed pattern of sufficient dimensions to permit removal of the plasma in a frozen state from the storage bag.

19 Claims, 3 Drawing Sheets

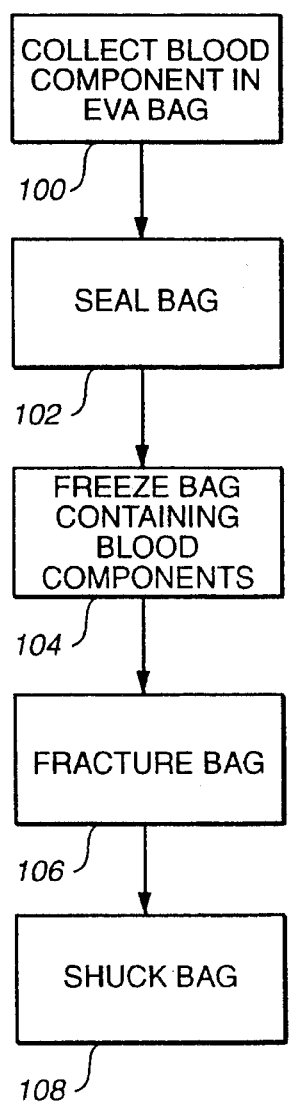
FIG._1
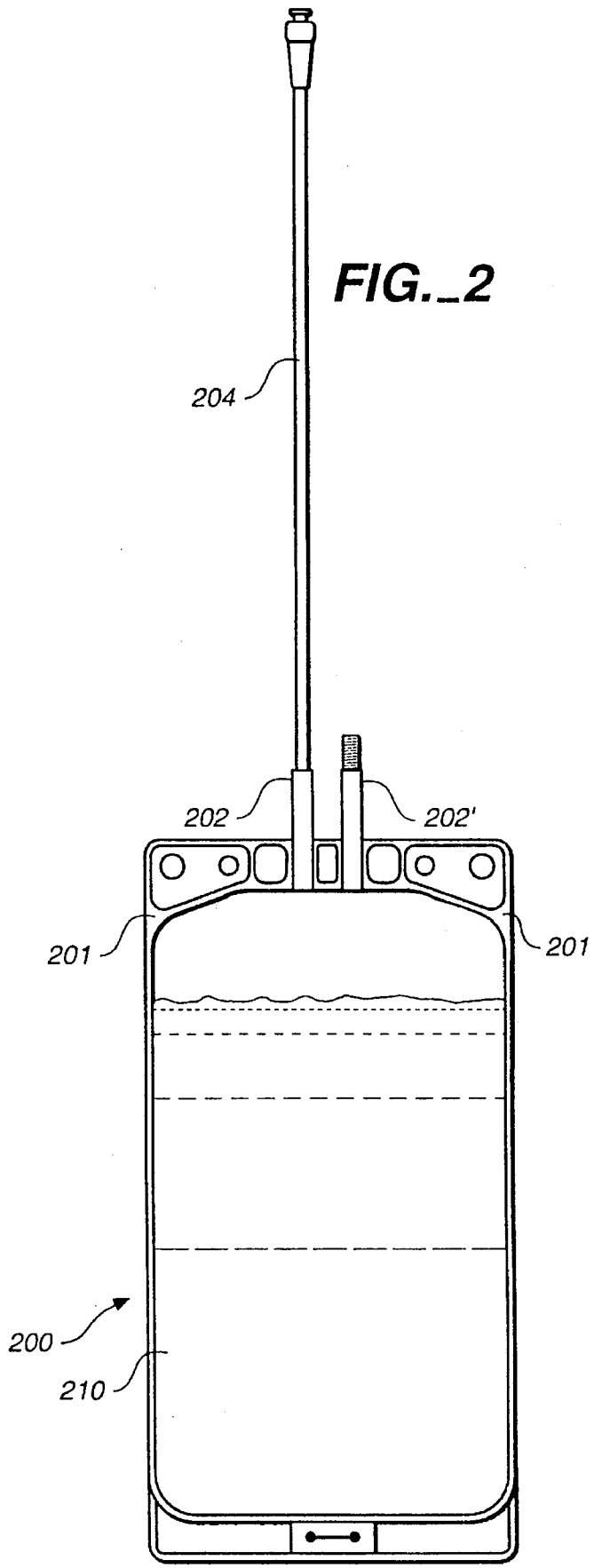
FIG._2

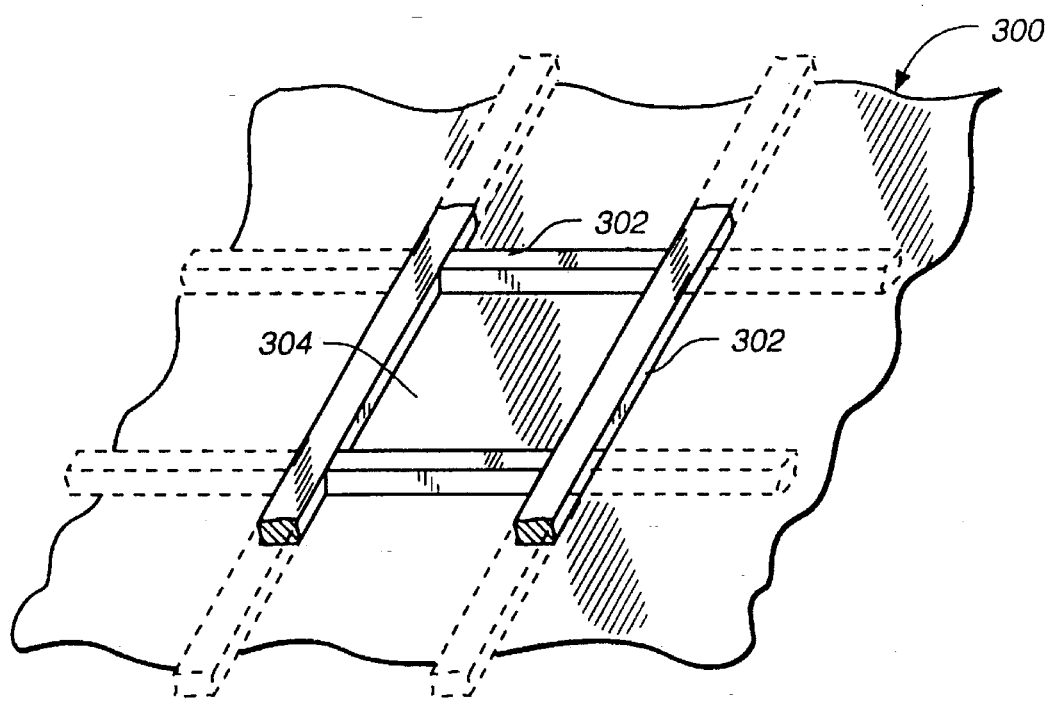
FIG._3A
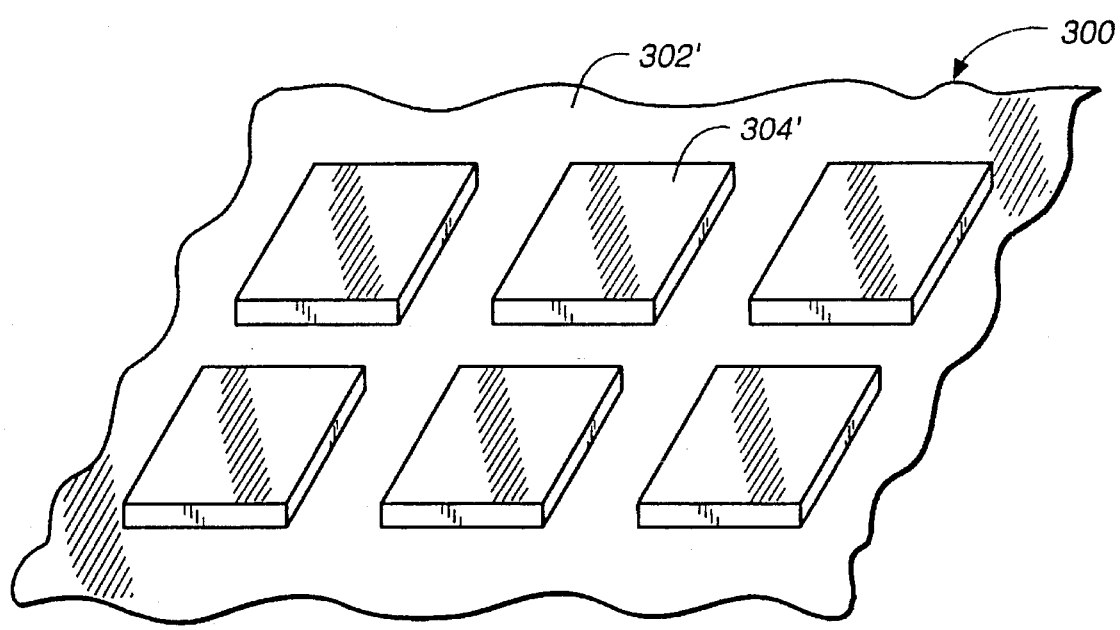
FIG._3B

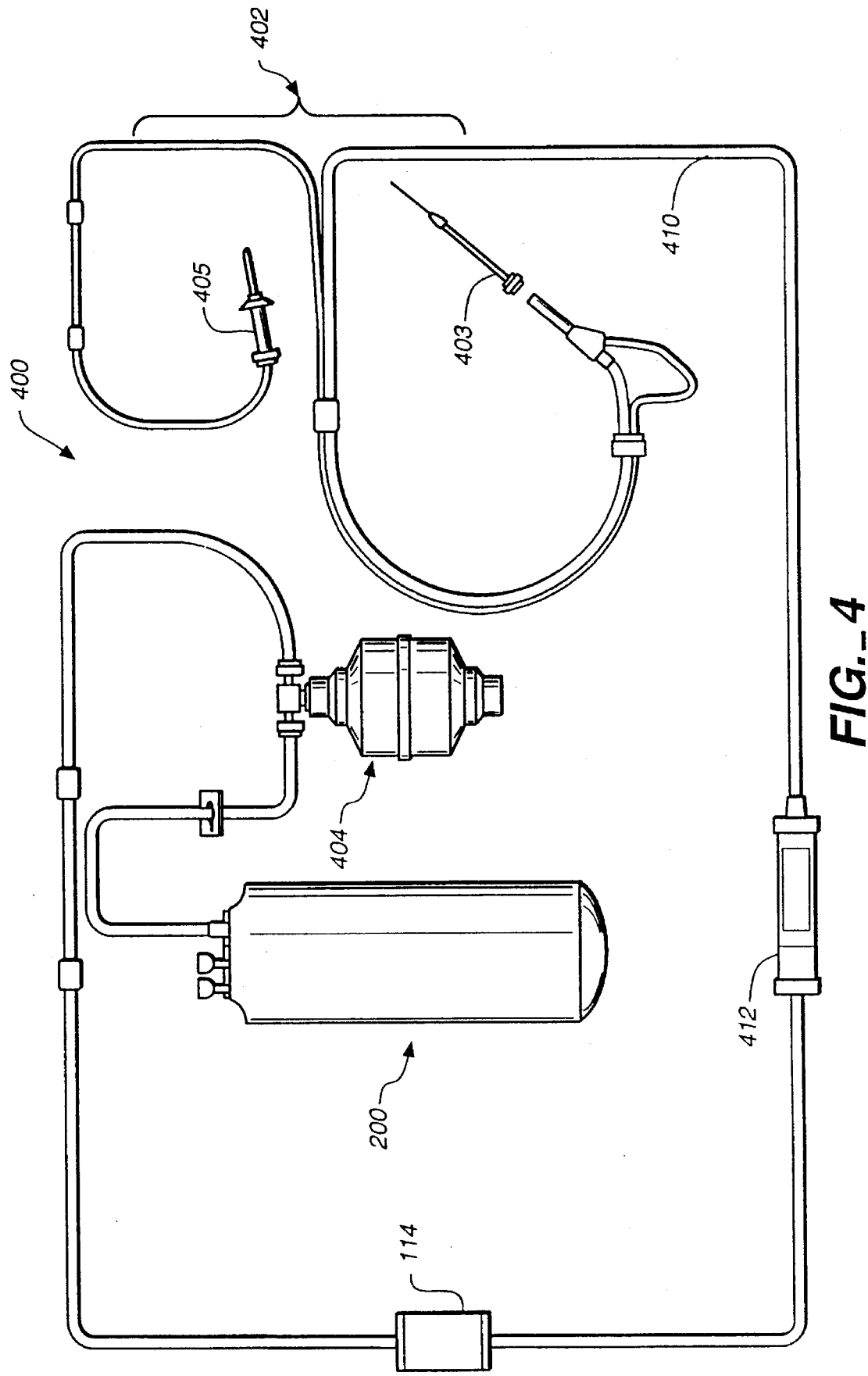
FIG._4

METHOD AND SYSTEM FOR COLLECTING, PROCESSING, AND STORING BLOOD COMPONENTS

CROSS-REFERENCE TO RELATED APPLICATIONS

This application is a divisional of application Ser. No. 08/123,521, filed Sep. 17, 1993, now abandoned.

BACKGROUND OF THE INVENTION

1. Field of the Invention

The present invention relates to plastic bags used for the collection, processing, and storage of blood products, such as plasma. Specifically, the invention relates to an ethylene vinyl acetate bag used in the collection of human plasma, freezing the plasma after collection, storing the frozen plasma, and subsequent processing.

2. Description of Background Art

Current containers used for plasma storage and processing are of two principle types: (1) a polyvinyl chloride (PVC) flexible bag, or (2) a rigid or semi-rigid blow molded olefin bottle or bag.

PVC bags have been used for decades for freeze storing plasma, and have the advantages of efficient manufacturability, low container cost, and good blood compatibility. However, significant disadvantages also exist with this type of container. The most significant disadvantage is the fragility of the container when frozen. The glass transition temperature ($T_g$), or temperature at which the film changes from flexible to brittle, is higher than the freezing temperatures commonly used for plasma.

This means that the bag is flexible and relatively strong at room temperature, but becomes excessively brittle or glass-like when frozen. This fragility leads to some percentage of the bags breaking during storage and handling. Bag breakage is undesirable since it allows for potential contamination (bacterial, particulate, and the like) that can adversely affect the purity of products subsequently made from this plasma. Bacterial contamination, in particular, can adversely affect protein yields and quality during the fractionation process due to the release of proteolytic enzymes and pyrogens.

The PVC film used in the manufacture of the plasma bags presently on the market has routinely been manufactured using the plasticizer di-2-ethyl-hexyl phthalate (DEHP). Considerable amounts of DEHP are leached from the walls of the blood bags by the plasma during storage. Recently, concern has been raised over the potentially harmful effects of DEHP in blood products chronically transfused to patients.

A common method for removing plasma in a frozen state from PVC storage bags is fracturing the bags at cryogenic temperatures, followed by shucking the bag from the frozen plasma. That process involves dipping the entire bag and contents into liquid nitrogen. The frozen bag then is shattered, for example by dropping the frozen bag onto a surface from a distance. The frozen plasma or blood component then is removed, using a process known as "shucking", from the shattered bag fragments.

During the shucking step, when the bag fragments are removed from the plasma "pellet", often some plasma sample is lost due to adherence to the inside of the bag. The bag, thus, should not adsorb any of the plasma, but should permit the total release of ail plasma from the bag walls.

By contrast, olefin bottles and bags typically are break resistant while frozen, but are otherwise difficult to open. Olefin bags do not readily shatter using the liquid nitrogen process described above. The process required to remove plasma from frozen olefin bags and bottles involves the time consuming and cumbersome thawing, or "skin thawing", process. This process involves partially thawing the frozen bag and plasma until the bag lifts away from the plasma surface. This process potentially degrades the desired proteins contained in the frozen plasma. Further, since the olefin bottles are not flexible they require substantial storage space due to bulk of the containers.

Medical solution bags are available on the market that are manufactured from high concentrations of ethylene vinyl acetate. For example, one such bag contains approximately 18% vinyl acetate per total polymer content. However, such bags are not useful for the fracturing process outlined above, since plasma adheres to the walls of the bags. Thus, it is difficult to get a complete extraction of plasma from bags having a high vinyl acetate content, i.e., a content above 18% vinyl acetate per total polymer content, resulting in significant loss of product due to losses of plasma adhering to discarded film fragments.

Ethylene vinyl acetate films with vinyl acetate contents below 9% have suitable plasma release characteristics during the cryogenic fracturing process. However, these films do not readily form into plasma bags since they do not form good radio frequency seals due to the lack of sufficient polarity in the polymer structure. This lack of sufficient molecular polarity is due to the low level of the vinyl acetate component in the film structure. Radio frequency (RF) sealing is the preferred method of bag manufacture due to its known efficiency and ability to produce water-tight, high-pressure seals.

Thus, there remains a need for a safe, effective method and bag for collecting, processing, and storing plasma and other blood protein components that permits complete recovery of the plasma sample from within the bag during a cryogenic fracturing process.

SUMMARY OF THE INVENTION

The present invention involves a flexible, cryogenically openable ethylene vinyl acetate (EVA) bag where the vinyl acetate component comprises between 9% and 18% of the total EVA co-polymer. The bag may have an embossed inner surface to facilitate removal of the cryogenically preserved sample, or pellet, from the bag, as described in further detail below.

The inventive method involves collecting plasma or another blood component in a flexible bag manufactured from ethylene vinyl acetate EVA wherein the vinyl acetate is present in an amount of between about 9% and about 18% by weight of total EVA co-polymer. The EVA bag is sealed, and the plasma is frozen in the bag at a temperature of approximately −30° C. to form a substantially solid protein or plasma pellet contained in the bag. The bag then may be stored for a desired period of time at a sufficient temperature to maintain the pellet in a frozen state. The method then involves a cryogenic fracturing process, followed by a shucking process, to remove the pellet in its intact, frozen form from the bag. The intact, frozen pellet then may be further processed for separation of biological products.

The freeze fracturing process involves exposing the bag, together with its contents, to a temperature of approximately −180° C. The bag is fractured using one of a variety of methods known in the art to loosen the bag from the pellet. The intact, frozen pellet then may be removed from the bag fragments. The ethylene vinyl acetate (EVA) material breaks into large, relatively intact sections, with little debris.

The invention further includes a plasma storage bag, having at least one port in communication with a plasma source, for introducing plasma into the storage bag. The inner surface of the storage bag may include a pattern, such as an etched or embossed pattern, of sufficient dimensions so as to enhance the removal of the plasma in a cryogenic state from the storage bag. The pattern preferably is a plurality of shapes, which may include an embossed portion that may be either a raised shape or raised cross-hatches.

The port may be manufactured by co-extruding ethylene vinyl acetate (EVA) with polyvinyl chloride (PVC), to form a port having an outer surface of EVA and an inner surface of PVC. The port thus may be integrated with an EVA bag body of the type described above and may be capable of receiving standard PVC tubing. Preferably, the port has a cross-sectional composition of at least about 60% total EVA co-polymer.

The present invention also is a plasmapheresis system having a blood processing system, including a blood collection system and a separation system for separating the plasma from the cells in the collected sample. The invention includes a plasma storage bag, in communication with the separation system, for receiving the plasma and manufactured from ethylene vinyl acetate (EVA). The pheresis system may include at least one port, in communication with the separation system and the plasma storage bag, for introducing the plasma from the separation system into the plasma storage bag. The port preferably is co-extruded with EVA and PVC, such that the outer EVA layer is 60% of the thickness of the port.

BRIEF DESCRIPTION OF THE FIGURE

FIG. 1 is a flow chart illustrating the inventive method.

FIG. 2 is a front elevation view of an exemplary EVA plasma bag that may be used in practicing the present invention.

FIGS. 3A–3B show exemplary patterns of an embodiment of the present invention.

FIG. 4 is an exemplary plasmapheresis system embodying the present invention.

DETAILED DESCRIPTION OF THE PREFERRED EMBODIMENTS

The present invention involves a method of collecting, processing, and storing blood components, such as plasma, in an ethylene vinyl acetate (EVA) bag, and specific co-polymer bags that may be used in conjunction with the inventive method. The invention also involves an improved plasmapheresis system including a plasma bag comprising 9%–18% vinyl acetate by weight of total EVA co-polymer, and having a patterned inner surface.

There are certain advantages to using EVA co-polymer material for such storage bags over using conventional PVC co-polymer material. One such advantage is that there is no apparent leaching of plasticizer from the EVA bag into the blood component contents. As described above, a recently-discovered problem with the PVC bags is leaching of DEHP into the bag contents. Furthermore, EVA has a low adsorption of protein components so that recovery of protein components from an EVA bag is higher than with PVC bags.

For purposes of the following discussion, plasma is cited as the preferred blood component. However, other blood components, such as platelets, may be suitable for use in conjunction with the method and system described herein.

FIG. 1 is a flow chart illustrating the method of the present invention. The method generally involves the steps of collecting 100 the blood component into a flexible bag manufactured from EVA, then sealing 102 the bag to secure the blood component in the bag. The bag, with its contents, next are frozen 104 by exposing the bag to a temperature at least as low as −30° C. to form a substantially solid pellet within the bag. In one embodiment, the pellet is stored at a sufficient temperature to maintain the pellet in a frozen state. The pellet may be removed from the bag in a substantially solid, frozen form by first fracturing 106 and then shucking 108 the bag. The bag may be shipped after the freezing step 104 and prior to the fracturing step 106.

A preferred form of the storage bag 200 is shown in FIG. 2. The bag 200 may be substantially any shape, preferably having a shape that optimizes the surface area of the contents for freeze storage.

In the illustrated embodiment, the corners 201 of the bag 200 are rounded to minimize the fracture of the frozen pellet 210 during transport, storage, and handling to avoid breaking the bag. Sharp corners on bags tend to cause damage to the bag 200, particularly during shipping and handling, since broken pellet fragments are sharp if fractured and may pierce the bag. In a preferred form of the bag 200, at least one port 202 is included to connect the bag 200 to a fill source (not shown) of blood component. One port 202 may be connected to a flexible tubing 204 that enables distal connection of other bags, fill sources, and the like.

The storage bag 200 preferably is flexible to facilitate storage, both in the empty and filled states. By minimizing the amount of space the bag 200 occupies during storage, shipping, and the like, the cost of collecting, processing, and storing blood protein components may be reduced.

A preferred polymer bag 200 used in practicing the inventive method is manufactured using an ethylene vinyl acetate (EVA) co-polymer. A preferred range of the vinyl acetate content is about 9% to about 18% by weight of total EVA co-polymer, most preferably a vinyl acetate content of approximately 12 percent by weight of total EVA co-polymer. Other than having an EVA composition, the bags 200 are manufactured in the same manner as other polymer and co-polymer bags. For example, the bag may be manufactured from a single sheet of material, from two sealed sheets of material, from a collapsed blown bubble of material, and the like. The material preferably is extruded, but may be formed by other appropriate methods known in the art.

As mentioned above, co-polymer bags manufactured with a vinyl acetate content of over 18% by weight of total EVA co-polymer are less desirable because plasma adheres to the bag surface. In such bags, recovery of proteins, such as plasma, is reduced since some of the plasma remains attached to the bag. On the other hand, if a co-polymer bag is manufactured with a vinyl acetate content of less than 9% by weight of total EVA co-polymer, there may be a problem with manufacturing the bag using radio frequency (RF) signals. That is, the resulting RF seals may not remain water-tight. Although other methods of manufacturing a sealed plastic bag, specifically a plasma bag, are available, the use of RF sealing is the preferred form in the industry. An RF seal is clean, efficient, and strong. However, absent a sufficient molecular polarity as provided by the vinyl acetate, RF signals may be relatively ineffective.

In a preferred form of the present invention, and as shown in FIGS. 3A–3B, the co-polymer bag 200 includes a predetermined pattern etched or embossed on the inner surface 300 of one or both sides of the bag. In the illustrated embodiments, the patterns include raised cross-hatchings 302 or raised areas 304'. The pattern may have several forms, such as a diamond, rectangular, square, or other polygonal shapes formed by the cross-hatchings. A surprising discovery is that if the lines 302, 302' of the pattern are too close together, the plastic bag 200 does not readily and completely peel away from the pellet 210 during the shucking step 108. However, if the pattern lines 302, 302' are too far apart, a similar difficulty during shucking 108 arises.

In a preferred form of the invention, the raised portion 304' of the pattern covers at least one quarter of the raised surface area of the inner surface of each bag side. In the embodiment having a diamond or rectangular shaped pattern, the raised portions 304' preferably are approximately 0.35 mm×0.6 mm in dimension. Other patterns and specific dimensions may be appropriate and may depend on the specific composition of the bag 200, the manufacturing capabilities, design considerations, and the like.

Embossing or etching a pattern on the inner surface of the bag 200 has surprisingly been found to improve the amount of plasma recovered during the shucking step 108, as described above. Although shucking non-embossed bags does result in the collection of plasma, often the recovery is less than for embossed bags. In addition, the patterned surface, particularly the embossed portion, reduces adherence of the inner bag walls to each other during fabrication, storage, and shipping of the bags, prior to introduction of plasma and minimizes the amount of pressure required to open the bag 200 in use.

The ports 202, 202' of the illustrated embodiment of the present invention preferably are co-extruded with EVA and PVC. The ports 202, 202' include an outer surface material of EVA and an inner surface material of PVC. Using ports 202, 202' of this particular EVA/PVC composition, it is possible to co-mingle, RF weld, or otherwise integrally form the port 202 with the EVA bag body. In a preferred embodiment, the ports have an EVA content of about 60% of the radial thickness of the port. The inner PVC surface enables formation of a solvent bond, or other type of bonding, with an external PVC tube (e.g., tubing 204 of FIG. 2). The use of at least one port 202 having such a composition optimizes the attaching of the bag 200 to external sources, improving the ability to maintain a closed system. It may also be possible to remove the tubing 204 and seal the port 202, after filling the bag, resulting in an EVA bag having a minimal amount of PVC and thus is "cold friendly", maintaining its properties when exposed to temperatures of less than about –30° C. for extended periods of time.

After collecting 100 the protein in the bag 200, the bag 200 may be sealed 102 using any method known to those skilled in the art. For example, as discussed above, the bag closure may be an RF seal. The bag 200 next is exposed to a temperature sufficient to freeze 104 the plasma to a substantially solid form. Preferably, the temperature at the freezing step 104 is at least as low as –30° C. This freezing step 104 may be accomplished by placing the bag 200 into any freezer environment or in any other manner known to those skilled in the art.

Once the bag and its contents are frozen, the entire assembly may be stored for subsequent use. The bags 200 may be maintained in an environment that sustains a minimum temperature sufficient to maintain the pellet 210 in a frozen state in the bag 200. The length of storage depends on end-user requirements.

There are several methods available for removing the frozen pellet 210 from the EVA bag 200. The preferred method is a cryogenic fracturing process that involves dipping the entire bag 200, including the frozen pellet 210, into a container of liquid nitrogen for several seconds. The bag 200 next is mechanically fractured 106, or otherwise disrupted, for example by impact with a solid surface. Upon impact, the bag cracks, allowing shucking 108 of the intact, solid frozen pellet. Other exemplary methods of fracturing 106 the bag include using gravity to crack and pull the bag 200 away from the pellet, chopping, peeling, or cutting the bag 200 away from the frozen pellet. In one embodiment, following the freezing step 104, the bag 200 may be sent to a fractionator prior to shucking 108.

In another embodiment of the invention, the EVA bags are used in conjunction with a plasmapheresis system 400, as shown in FIG. 4. In that embodiment, a unit of blood is collected into a blood collection system 402 and a separator system 404. In the illustrated embodiment, the blood collection system 402 includes a needle assembly 403 and an anticoagulant assembly 405, connected by tubing 410. The system 400 may also include a return filter 412, to remove any clots, and a pressure monitoring bag 414. Blood is drawn from a blood source (not shown), using the collection system 402, and then passed through the separator system 404 to separate the plasma component from the cell component of the collected blood. In a preferred embodiment, the plasma component is collected into the plasma collection bag 200 of the type described above. The separator system 404 may include a centrifuge bowl (as illustrated in FIG. 4) or any type of filter system presently commercially available.

The invention is further described by the following non-limiting example.

EXEMPLIFICATION

Plasma is collected into EVA plasma collection bags having approximately 12 percent vinyl acetate by weight total EVA co-polymer. After the plasma collection, the bags are sealed off, frozen at about –30° C., and packaged for shipping or storage.

The bags then are removed from around the frozen plasma pellet. Removal occurs by immersing the frozen bags in a cryogenic substance, such as liquid nitrogen, for nominally 10 seconds, followed by quick manual separation of the frozen plasma unit from the fractured bag. The EVA bag tends to remain together when fractured, thus minimizing small pieces of plastic in the pool. The bag tends to fracture in the center, with the top and bottom remaining intact. The mechanics of the shucking tends to be peeling the top and bottom of the bag away from and off of the plasma pellet.

Although the discussion above indicates plasma as the preferred blood component, it should be understood that other blood components, proteins, solutions, liquids, and the like may be suitable for use in conjunction with the present method and system. The bag also may be used for collecting, processing, or storing such other products. Other variations will be apparent to one skilled in the relevant art.

In practicing the present inventive method, the plasma may be collected in any method known to those skilled in the art. For example, the EVA bags may be used in conjunction with a plasma collection system generally known and available to those skilled in the art. Essentially cell-free plasma preferably is used in the present system, however, other blood components may be used in conjunction with the inventive bag and method. Any component or product of which it is desirable to store frozen for subsequent removal may benefit from the present invention, particularly those components which would otherwise adsorb/adhere to plastic bags of a standard composition or are of high monetary value and would benefit from storage in a tough, break-resistant bag.

Although the foregoing invention has been described in some detail by way of illustration and example for purposes of clarity of understanding, it will be obvious that certain changes and modifications may be practiced within the scope of the invention claimed herein.

What is claimed is:

1. Method of collecting, storing, and processing protein components from blood, comprising:
   A. collecting the protein components in a flexible bag manufactured from ethylene vinyl acetate (EVA), wherein vinyl acetate is present in an amount of between about 9 and about 18 percent by weight of total EVA;
   B. sealing the bag;
   C. exposing the bag to a temperature at least as low as about −30° C. to form a substantially solid protein pellet therein;
   D. fracturing the bag; and
   E. removing the solid protein pellet in an intact, frozen form, from the bag.

2. The method of claim 1, including exposing the bag to a mechanical impact sufficient to disengage the bag from the solid protein pellet.

3. The method of claim 1, wherein fracturing the bag comprises exposing the bag to a cryogenic substance.

4. The method of claim 1, wherein the protein component is plasma, the method further comprising, prior to collecting the protein components in the flexible bag, separating the plasma from whole blood.

5. The method of claim 1, wherein the vinyl acetate is present in an amount of between about 9 and about 12 percent by weight of total EVA.

6. The method of claim 1, wherein the vinyl acetate is present in an amount of between about 12 and about 18 percent by weight of total EVA.

7. The method of claim 1, wherein the flexible bag further comprises at least one port, in communication with a blood source, the port comprising an outer port surface material including an ethylene vinyl acetate (EVA) and an inner surface material including a polyvinyl chloride (PVC), the method further comprising:
   prior to collecting the protein components in the flexible bag, attaching a tubing, including a polyvinyl chloride (PVC), to the port.

8. The method of claim 7, wherein sealing the bag further comprises:
   detaching the tubing from the port; and
   sealing the port.

9. The method of claim 7, wherein the outer port surface material comprises at least about 60 percent EVA radial thickness.

10. The method of claim 1 wherein the bag includes an inner surface, said surface having a predetermined pattern that permits separation of the solid pellet from the surface after fracturing the bag.

11. The method of claim 10, wherein the pattern comprises an embossed portion.

12. The method of claim 10, wherein the pattern includes raised cross-hatches.

13. A method of processing blood products, comprising:
   collecting a blood product in a flexible bag manufactured from ethylene vinyl acetate (EVA), wherein vinyl acetate is present in an amount of between about 9 and about 18 percent by weight of total EVA;
   sealing the bag;
   freezing the blood product to form a substantially solid frozen blood product;
   opening the bag; and
   removing the solid product, in frozen form, from the bag.

14. The method of claim 13 wherein opening the bag includes fracturing the bag.

15. The method of claim 13 wherein the bag includes an inner surface, said surface having a predetermined pattern that permits separation of the solid product from the surface after opening the bag.

16. The method of claim 13, wherein the pattern comprises an embossed portion.

17. The method of claim 13, wherein the flexible bag further comprises at least one port, in communication with a blood source, the port comprising an outer port surface material including an ethylene vinyl acetate (EVA) and an inner surface material including a polyvinyl chloride (PVC), the method further comprising:
   prior to collecting the product in the flexible bag, attaching a tubing, including a polyvinyl chloride (PVC), to the port.

18. The method of claim 13, wherein the vinyl acetate is present in an amount of between about 9 and about 12 percent by weight of total EVA.

19. The method of claim 13, wherein the vinyl acetate is present in an amount of between about 12 and about 18 percent by weight of total EVA.

\* \* \* \* \*